United States Patent [19]

Janssen

[11] Patent Number: 5,200,453
[45] Date of Patent: Apr. 6, 1993

[54] PRESERVATIVE FOR OPHTHALMIC SOLUTIONS

[75] Inventor: Herwig J. Janssen, Beersebaan, Belgium

[73] Assignee: Iolab Corporation, Claremont, Calif.

[21] Appl. No.: 583,523

[22] Filed: Sep. 17, 1990

[30] Foreign Application Priority Data

Sep. 18, 1989 [GB] United Kingdom ............... 8921072

[51] Int. Cl.$^5$ .......................................... A61K 31/415
[52] U.S. Cl. .................................... 514/399; 514/912; 514/913; 514/914; 514/915; 548/341.1
[58] Field of Search ............... 548/341; 514/399, 913, 514/914, 915, 912

[56] References Cited

U.S. PATENT DOCUMENTS 3,991,202 11/1976 Janssen et al. .................. 548/341
4,888,168 12/1989 Potts et al. ...................... 514/914

Primary Examiner—Floyd D. Higel
Assistant Examiner—Lenora Miltenberger
Attorney, Agent, or Firm—Benjamin F. Lambert

[57] ABSTRACT

An ophthalmic formulation comprising a salt of sepazonium or a similar imidazolium compound as a preservative is provided.

7 Claims, 1 Drawing Sheet

BENZALKONIUM CHLORIDE

FIG-1  BENZALKONIUM CHLORIDE
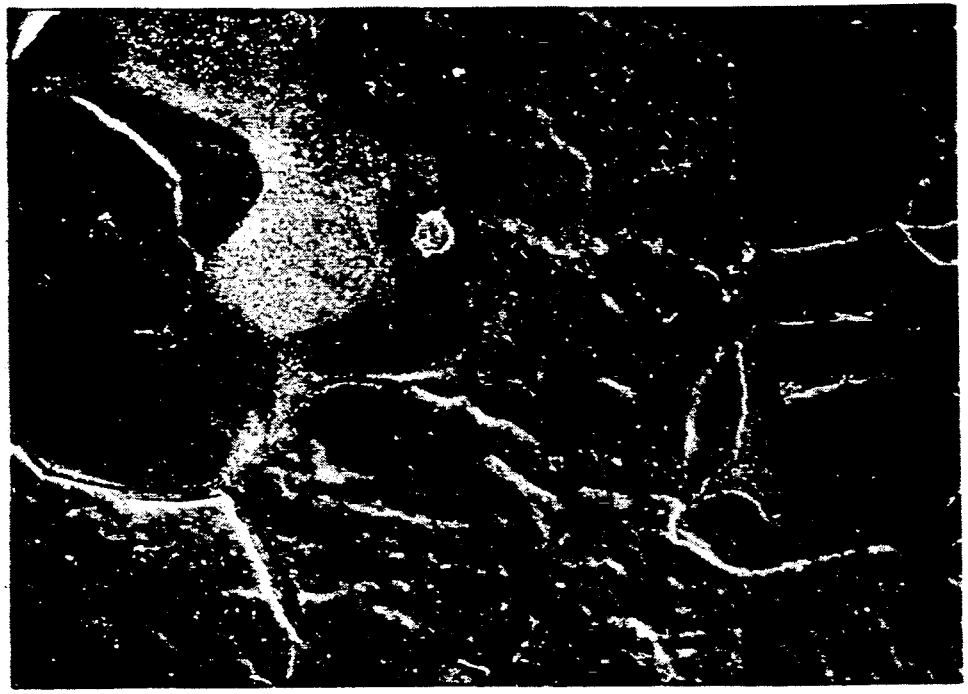
FIG-2  SEPAZONIUM

PRESERVATIVE FOR OPHTHALMIC SOLUTIONS

The subject invention is generally related to preservatives used in ophthalmic solutions and, more particularly, to the use of sepazonium chloride or similar compounds as a preservative in an ophthalmic solution.

Sepazonium chloride is a quaternary imidazolium derivative having the following structural formula:

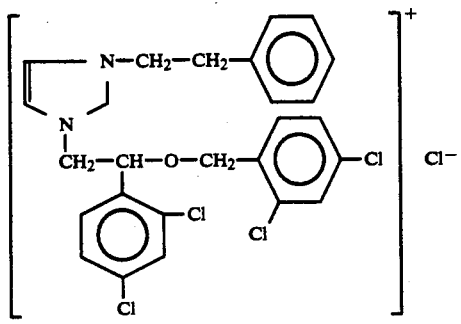

The IUPAC chemical name for sepazonium chloride is 1-[2,4-dichloro-β-(2,4-dichlorobenzyloxy)phenethyl]-imidazolium chloride. Sepazonium chloride is available from Janssen Pharmaceutica of Beerse, Belgium.

U.S. Pat. No. 3 991 202 discloses that imidazolium salts, such as sepazonium chloride, are useful as antimicrobial agents. U.S. Pat. No.3 991 202 discloses that imidazolium salts can control such organisms as *Microsporum canis, Trichophyton mentagrophytes, Trichophyton rubrum, Phialaphora verrucosa, Cryptoccus neoformans, Candida tropicalis, Candida albicans,* Mucor species, *Asperiqillus fumigatus, Sporotrichum schenkii,* Saprolegnia species, *Salmonella pullorum gallinarum, Escherichia coli, Pseudomonas aeruginosa, Erysipelothrix isidiosa, Staphylococcus hemolyticus* and *Streptococcus pyrogenes.* Concentrations ranging between 0.1 and 10% by weight of the imidazolium salt were found effective for combatting both fungi and bacteria.

Ophthalmic solutions are formulated to have the following attributes: long shelf-life, effective antimicrobial activity, comfort for the patient, penetrability of the active agents and minimal side effects. Tissue reactions from these preparations are often tolerated to gain one or more of the specific benefits. However, there are frequent situations when specific drug components may induce serious iatrogenic diseases, possibly vitiating any beneficial effects on the primary disease process.

Benzylalkonium chloride (BAK) is the most widely used preservative in ophthalmic solutions today. BAK is a powerful cationic detergent which destroys bacteria after ionic attraction. Pfister et al., in *Invest. Ophthalmol.,* 15, 4, pages 246-259, April 1976, found that BAK-containing preparations can cause severe plasma membrane disruptions and cell death in the cornea. Pfister et al. used scanning electron microscopy (SEM) to study the effect of topical drugs, vehicles and preservatives (i.e. BAK) on the surface corneal epithelium. Treatment of the cornea with a 0.01 percent solution of BAK resulted in the top two layers of cells being desquamated. When cell death occurred, severe membrane disruption was accompanied by loss of microvilli and rupture of intercellular tight junctions. Pfister et al. found frequent use of BAK-containing preparations can act as an iatrogenic impediment to the epithelial healing process and can shorten the tear film break up time.

Burstein et al., in *Invest. Ophthalmol. Vis. Sci.,* 16, 10, pages 899-911, October 1977, used continuous electrophysiologic monitoring and SEM to study the effects of very low concentrations of preservatives (e.g. BAK, thimerosal and amphotericin B) on the cornea. Burstein et al. found that BAK, at a concentration as low as 0.01%, briefly increased ion transport, then greatly decreased epithelial resistance with severe disruption of surface cell layers occurring simultaneously with the decrease in resistance. Burstein, in *Invest. Ophthalmol. Vis. Sci.,* 19, 3, pages 308-313, March 1989, found BAK causes a progressive increase in damage to corneal epithelial cells at concentrations between 0.001% and 0.01%, as determined by SEM.

BAK is commercially used in ophthalmic solutions at concentrations ranging between 0.004% and 0.02%. The SEM investiqations noted above reveal that some epithelial surface cell damage will result at lower concentrations and extensive damage will result at higher concentrations. A need exists for a preservative, which will be used in ophthalmic preparations, that does not adversely affect the corneal epithelial cells. The dates of the articles (e.g. 1976) suggest that this need has existed for several years and has not been satisfied.

It is therefore an object of this invention to provide a preservative for ophthalmic solutions which is as effective as BAK, but which does not cause the epithelial cell damage associated with BAK.

Accordingly, the present invention provides an ophthalmic formulation comprising as a preservative a phamaceutically acceptable imidazolium salt of formula I

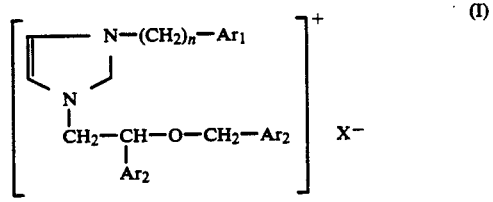

wherein:

n is an integer from 1 to 6;

$Ar_1$ is phenyl or phenyl substituted with 1, 2 or 3 halo, $C_1$-$C_6$ alkyl or $C_1$-$C_6$ alkoxy groups;

each $Ar_2$ is independently a phenyl group substituted with two halo groups; and X is a pharmaceutically acceptable anion.

Preferably, n is an integer from 2 to 4 and most preferably is 2.

$Ar_1$ is preferably an unsubstituted phenyl group.

The halo groups substituting the phenyl group for $Ar_2$ may be fluoro, chloro, bromo or iodo. Preferably, the halo groups are chloro groups.

Preferably X is a halide anion, such as a fluoride chloride, bromide or iodide anion. Most preferably, the anion is a chloride anion.

Most preferably the imidazolium salt is sepazonium chloride.

The imidazolium salts of formula I can be utilized as preservatives in a wide variety of ophthalmic products including anti-infectives, steroidal and non-steroidal compositions, anti-inflammatories, decongestants, anti-glaucoma agents, irrigation compositions, diagnostic agents, artificial tear compositions, contact lens solutions and combination products of the above. These formulations can be in the form of solutions, suspensions, ointments or gels.

The imidazolium salts of formula I can be utilized in the above products in a range of from about 0.015% to about 03% by weight of the total composition. Amounts above about 0.03% by weight of the total composition may be found to be an irritant to the eye.

Experiments have been conducted which show that sepazonium chloride is an effective preservative, and that use of sepazonium chloride in ophthalmic solutions is safer than the use of a BAK in ophthalmic solutions. The experiments included a guinea pig sensitization test, a preservative effectiveness test and a comparative eye damage investigation.

Results from the guinea pig sensitization test showed that sepazonium chloride has no propensity for contact sensitization. It can be concluded that the eye should not become sensitized to an ophthalmic solution containing sepazonium chloride.

The preservative effectiveness test was performed according to U.S. Pharmacopoeia guidelines. In particular, various concentrations of sepazonium chloride were tested to determine the lowest concentration which meets USP XXI, a U.S. Pharmacopoeia guideline requiring antimicrobial activity for five different pathogens which are harmful to the eye. The preservative effectiveness test showed that a 0.015% solution of sepazonium chloride meets USP XXI for antimicrobial effectiveness. A 0.02% solution of BAK, which is the concentration found most often in commercially available ophthalmic solutions, also meets the USP XXI guideline.

The comparative eye damage investigation employed SEM and light microscopy to evaluate corneal epithelial damage in New Zealand white rabbits caused by dosing with sepazonium chloride or BAK. Two groups of rabbits were randomly selected. In one group, each rabbit received drops of sepazonium chloride in one eye and drops of BAK in the other eye where the drops were administered according to a "mild usage" scheme. No significant difference in the effects of sepazonium chloride and BAK was found for this group. In another group, each rabbit received drops of sepazonium chloride in one eye and drops of BAK in the other, where the drops were administered according to an "exaggerated usage" scheme. Sepazonium chloride was found to be significantly less harmful to the corneal epithelial cells than BAK where the rabbits were subjected to exaggerated usage. It can be concluded that sepazonium chloride is a safer preservative than BAK in ophthalmic solutions.

The foregoing and other objects, aspects and advantages of the invention will be better understood from the following detailed description of a preferred embodiment of the invention with reference to the accompanying drawings in which:

FIG. 1 is a photolithographic reproduction of a rabbit cornea which was treated under exaggerated usage conditions with BAK; and FIG. 2 is a photolithographic reproduction of a rabbit cornea which was treated under exaggerated usage conditions with sepazonium chloride.

A living body can become sensitized to substances which come into repeated contact with body surfaces over an extended period of time. The Magnusson/Kligman Guinea Pig Maximization Test is an accepted method for testing a substance to determine its potential as a contact sensitizing agent. The complete procedure for the Magnusson/Kligman Guinea Pig Maximization Test is found in BCLT 01-21-02-009, Oct. 12, 1987 and that article is herein incorporated by reference.

Sepazonium chloride was tested for its sensitizing properties using the Magnusson/Kligman Guinea Pig Maximization Test. Sixteen female, outbred Hartley guinea pigs weighing between 300 and 500 grams were obtained from the Charles River Laboratories of Massachusetts. The guinea pigs were randomized into three treatment groups with one group being treated with sepazonium chloride, another group being treated with 10% formalin (positive control) and the last group being treated with a saline solution (negative control). On the first day of the study, three pairs of intradermal injections were made in the shoulder region of each animal. On the seventh day of the study, the animals were re-exposed to their respective solutions through direct 2×4 cm patches. The final challenge during the study occurred on the twenty first day of the study when a dose was applied on a 2×2 cm patch. On the twenty second day of the study, the patches were removed. On the twenty third day, the animals were examined for sensitization as evidenced by dermal reactions ranging from scattered, mild redness to intense red swelling.

There was no evidence of sensitization in either the sepazonium chloride treated animals or the negative control animals. All positive control animals were sensitized. It can be concluded that sepazonium chloride has no propensity for contact sensitization and may be classified as a Grade 1 (weak) sensitizer. During the study, the animals received Wayne guinea pig pellets and water ad libitum. No contaminants were known to exist in the food or water that would have affected the outcome of the study.

A preservative efficacy test was performed to determine the lowest concentration of sepazonium chloride which would meet the U.S. Pharmacopoeia guidelines for antimicrobial activity. The USP XXI preservative efficacy test specifies five different pathogens for which an antimicrobial agent should be effective and those organisms are *Staphylococcus aureus, Pseudomonas aeruginosa, Echerichia coli, Candida albicans,* and *Asperigillus niger*. These five pathogens are common eye irritants and are of the most concern for a preservative used in an ophthalmic solution. The microbial load, measured in terms of organisms per ml of product, and the survival level, measured in terms of percentage of viable organisms, were monitored over a twenty eight day test period. Table 1 shows the results obtained for the USP XXI preservatives effectiveness test.

TABLE 1

| Substance | Conc. (w/v) | Result |
|---|---|---|
| BAK | 0.02% | Meets USP XXI requirements for antimicrobial effectiveness. |
| Sepazonium Chloride | 0.03% | Meets USP XXI requirements for antimicrobial effectiveness. |
| | 0.025% | Meets USP XXI requirements for antimicrobial effectiveness. |
| | 0.02% | Meets USP XXI requirements for antimicrobial effectiveness. |
| | 0.015% | Meets USP XXI requirements for antimicrobial effectiveness. |
| | 0.01% | Not effective for *Pseudomonas aeruginosa* |
| | 0.005% | Not effective for *Pseudomonas aeruginosa* or *Escherichia* |

TABLE 1-continued

| Substance | Conc. (w/v) | Result |
|---|---|---|
| | | coli |

Microorganisms used in the preservative efficiency test were obtained from the American Type Culture Collection of Rockville, Md. The preservative efficacy test was performed on 0.02% BAK, the traditional concentration for BAK in ophthalmic solutions, to show the comparative effectiveness of sepazonium chloride. Table 1 shows that 0.015% sepazonium chloride is as effective as 0.02% BAK at destroying pathogens.

A comparative study using a modified Draize series was performed to compare the occulo-irritant effects of 0.015% sepazonium and 0.02% BAK. The damage to the corneal epithelium of a 0.015% sepazonium chloride solution q.i.d. was compared by SEM in four New Zealand white rabbits. Results from this study show that sepazonium chloride caused minimal changes to the corneal epithelium while BAK showed its very characteristic profile of corneal epithelial damage.

The visual evaluation used in the Draize test may not show corneal changes which result from acute usage. Therefore, a comparative evaluation was conducted using light microcopy and SEM to observe the corneal epithelial changes after treatment with either 0.02% BAK or 0.015% sepazonium chloride. The solution of 0.02% BAK was prepared by sequential dilution of a 1% BAK solution. The solution of 0.015% sepazonium chloride was prepared by sequential dilution of a 1% sepazonium chloride solution. Sepazonium chloride raw material is available from Janssen Pharmaceutics of Beerse, Belgium.

New Zealand white rabbits were randomly assigned to two treatment groups of five animals each. A complete slit lamp evaluation with fluorescein showed the rabbits had normal, healthy eyes. The rabbits in Group 1 received two drops of 0.02% BAK in one eye and two drops of 0.015% sepazonium chloride in the fellow eye every thirty minutes for a total of four doses (mild usage). The rabbits in Group 2 received two drops of 0.02% BAK in one eye and two drops of 0.015% sepazonium in the fellow eye every three minutes for a total of twenty doses (exaggerated usage).

Twenty minutes after the rabbits received their last eye drops, the rabbits were sacrificed and the globes were immediately enucleated and fixed with ½ Karnovsky's fixative. The corneas were removed and allowed to sit for thirty minutes in fixative. Processing for both SEM and light microscopy was accomplished by using a pick shaped wedge placed in fresh fixative. A rating system proposed by Burstein in *Invest. Ophthalmol. Vis. Sci.*, March 1980, pages 308-313, was used to evaluate the SEM photographs for corneal epithelial damage. Table 2 shows the rating system assigning a numerical score of 0-5 depending on the severity of the damage as evidenced by loss of microvilli, cell shrinkage (wrinkling), loss of hexagonal shape (rounding), retraction of cell junctions, peeling of cells and areas of desquamation.

TABLE 2

| Score | Description |
|---|---|
| Numerical Evaluation of Damage to Corneal Surface | |
| 0 | No visible damage seen by SEM; less than 2% of cells peeling; no wrinkling or smooth membrane; normal microvilli. |
| 1 | Some wrinkling or smoothing of cell surface; reduced numbers of microvilli on cells seen as "dark" at low magnification. |
| 2 | Prominent wrinkling and flattening of most cell surfaces; little peeling of cell borders observed. |
| 3 | Cell peeling and lifting of older, dark cells apparent; top cell layer without major disruption. |
| 4 | Top cell layer exfoliating, second layer intact beneath; preventing long term compromise of barrier properties. |
| 5 | Second cell layer peeling beneath first, revealing membranes of third layer, physiological resistance of corneal epithelium severely compromised. |

In Group 1, the mean damage score for BAK-treated eyes was 1.2±0.12 and the mean damage score for sepazonium chloride-treated eyes was 1.2±0.26. The two scores were not significantly different.

In Group 2, all pairs of eyes demonstrated less epithelial damage with sepazonium chloride as compared to BAK. The mean damage score for sepazonium chloride-treated eyes was 2.9±0.4 and the mean damage score for BAK-treated eyes was 4.0±0.16. The mean damage score for sepazonium chloride is significantly (p=0.02) less than the score for BAK. when compared to phosphate buffered saline (PBS)-treated eyes (control vehicle), Group 2 BAK-treated eyes showed significantly more damage (p=0.002), while Group 2 sepazonium chloride-treated eyes were not significantly different than PBS controls.

Contrasting FIGS 1 and 2, one can see that less epithelial damage is evident in the cornea treated with sepazonium chloride than the cornea treated with BAK.

Light microscopy with hematoxylin and eosin staining corroborated the pathologic changes seen with SEM.

While the invention has been described in terms of the preferred embodiments, those skilled in the art will recognize that slight variations in the form and concentration of the preservative can be made within the spirit and scope of the invention.

I claim:

1. A method for preserving Ophthalmic solutions which comprises adding to the solution an effective amount of a quaternary imidazolium salt of the formula:

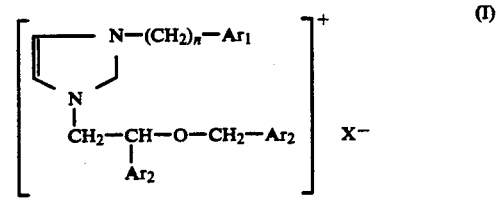

Wherein
n is an integer from 1 to 6;
Ar$_1$ is phenyl or phenyl substituted with 1, 2, or 3 halo, C$_1$-C$_6$ alkoxy groups;
X is a pharmaceutically acceptable anion; and each Ar$_2$ is independently a phenyl group substituted with two halo groups.

2. The method of claim 1 wherein the quaternary imidazolium salt comprises from 0.015% to 0.03% by weight of the total composition.

3. The method of claim 1 wherein n in the formula is an integer from 2 to 4.

4. The method of claim 1 wherein $Ar_1$ in the formula is an unsubstituted phenyl group.

5. The method of claim 1 wherein X in the formula is a chloride anion.

6. The method of claim 1 wherein the imidazolium salt is sepazonium chloride.

7. The method of claim 1 wherein the ophthalmic solution is selected from anti-infectives, steroidal and non-steroidal compositions, anti-inflammatory compositions, decongestants, anti-glaucoma agents, irrigation compositions, contact lens solutions, diagnostic agents and artificial tear compositions.

* * * * *